(12) United States Patent
Goettel et al.

(10) Patent No.: US 6,494,923 B2
(45) Date of Patent: *Dec. 17, 2002

(54) AGENTS AND METHOD FOR PRODUCING TEMPORARY COLORATIONS OF KERATIN FIBERS

(75) Inventors: Otto Goettel, Marly; Aline Pirrello, Givisiez; Sandra Mettler, Montevraz, all of (CH)

(73) Assignee: Wella Aktiengesellschaft, Darmstadt (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/445,747

(22) PCT Filed: Feb. 26, 1999

(86) PCT No.: PCT/EP99/01236

§ 371 (c)(1),
(2), (4) Date: Dec. 9, 1999

(87) PCT Pub. No.: WO99/59528

PCT Pub. Date: Nov. 25, 1999

(65) Prior Publication Data

US 2002/0010969 A1 Jan. 31, 2002

(30) Foreign Application Priority Data

May 16, 1998 (DE) .......................... 198 22 199

(51) Int. Cl.$^7$ .............. A61K 7/13; D06L 3/00; D06L 3/10
(52) U.S. Cl. ............. 8/405; 8/431; 8/102; 8/659; 8/670; 8/423; 8/110; 8/111
(58) Field of Search .................. 548/366.1; 8/405, 8/423, 431, 573, 102, 110, 111, 659, 670

(56) References Cited

U.S. PATENT DOCUMENTS

| | | | |
|---|---|---|---|
| 2,319,547 A | * | 5/1943 | Kendall et al. |
| 3,441,563 A | * | 4/1969 | Weissel et al. |
| 4,218,432 A | * | 8/1980 | Watanabe et al. ........ 548/366.1 |
| 4,266,014 A | * | 5/1981 | Moelants et al. ........ 548/366.1 |
| 4,288,534 A | * | 9/1981 | Lemahieu et al. ....... 548/366.1 |
| 4,440,852 A | * | 4/1984 | Onishi et al. ............ 548/366.1 |
| 4,681,471 A | | 7/1987 | Hayduchok et al. .......... 401/34 |
| 5,217,709 A | * | 6/1993 | Lagrange et al. .............. 8/405 |
| 5,474,578 A | | 12/1995 | Chan et al. ..................... 8/431 |
| 5,626,633 A | * | 5/1997 | Roschger ....................... 8/506 |
| 5,719,288 A | * | 2/1998 | Sens et al. ..................... 8/568 |
| 6,143,898 A | * | 11/2000 | Etzbach et al. ................ 8/568 |

FOREIGN PATENT DOCUMENTS

| | | |
|---|---|---|
| DE | 38 42 774 C1 | 3/1990 |
| EP | 833314 A2 * | 4/1998 |
| GB | 1278621 * | 6/1972 |
| JP | 3-204640 | 9/1991 |

OTHER PUBLICATIONS

Houben–Weyl 5/1 D (4–th Edition, 1954), pp. 231 and 296.
"Chemie in Unserer Zeit" (Chemistry in Our Times) 1978, No. 1, pp. 1–11.
Annalen 574, 106 (1951), pp. 106–121.

* cited by examiner

Primary Examiner—Margaret Einsmann
(74) Attorney, Agent, or Firm—Michael J. Striker

(57) ABSTRACT

In the method of temporarily coloring and later decoloring hair a hair colorant is applied and allowed to remain on the hair for an exposure time of 10 to 45 minutes at 20 to 50° C. and then rinsed out. Then at a later time, as desired, the hair is decolorized. The aqueous hair colorant contains 0.01 to 5 percent by weight of at least one dye compound of formula (IV), or a physiologically tolerated salt thereof;

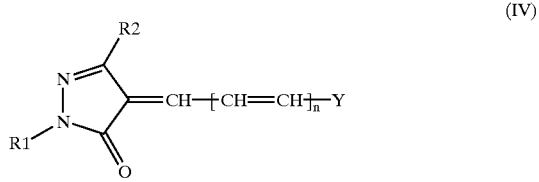

(IV)

wherein n=0, 1 or 2 and R1 represents a $C_1$- to $C_4$-alkyl group, a hydroxyethyl group, a dihydroxypropyl group, a methoxyethyl group, a carboxyethyl group, a $C_1$- to $C_4$-sulfoalkyl group, an unsubstituted or substituted phenyl radical with halogen, sulfonic or carboxylic acid substituents; R2 represents a hydrogen, a methyl group, a carboxylic acid group, a carboxylic acid group esterified with a $C_1$- to $C_4$-alcohol or a carboxamido group; and Y represents an aromatic five-membered heterocyclic ring, which may or may not be benzoanellated.

31 Claims, No Drawings

AGENTS AND METHOD FOR PRODUCING TEMPORARY COLORATIONS OF KERATIN FIBERS

BACKGROUND OF THE INVENTION

1. Field of the Invention

The present invention relates to nonoxidative colorants for keratin fibers, for example hair or wool, based on polymethine dyes and to a method for temporarily coloring keratin fibers, especially hair, whereby the color can be removed at any point in time.

2. Related Art

The coloring of hair is currently subject to the most varied trends. Whereas in the past hair was colored primarily to cover gray areas, today there is an increasing demand for integrating the hair color into current fashion as an expression of personality.

Now as before, two established methods of hair coloring are available. One of these is the oxidative hair coloring which a priori is unsuitable for temporary coloring, because it produces a very durable coloring result. The other method consists of the possibility of coloring hair with colorants containing nonoxidative, direct dyes (often referred to as toners). Although the dyes used for this purpose are optimized for dyeing performance as well as for remaining on the hair as long as possible, the color shade gradually weakens with every hair washing. Thus, depending on the product used and the type of hair, such colorants as a rule do not last more than a maximum of 10 hair washings. If the user of such nonoxidative colorants would like to restore her original hair color at an earlier time, no satisfactory means are currently available for rapidly restoring the original color shade, because the products used for this purpose are usually very aggressive and cause hair damage.

In the literature are described many attempts to restore the color of fibers. For example, German Patent DE 38 42 774 and U.S. Pat. No. 4,681,471 describe the decoloration of triarylmethane dyes with reducing agents. U.S. Pat. No. 5,474,578 uses the same approach whereby the dyes are decolorized by an oxidative or reducing treatment or a combination of these two treatments. A general problem underlying these methods is, in particular, that in most cases only partial decoloration is attained. Thus the method of U.S. Pat. No. 5,474,578 in the most favorable case produces at the most a degree of decoloration of 90 to 93%, and this degree of decoloration can be achieved only by applying a reductive treatment after an oxidative one. Such double treatment, however, causes extraordinary hair damage. Normally, such a method produces only partial (often <50%) hair decoloration.

The above-said patents also have in common that they deal with the decoloration of dye classes that have been used in hair cosmetics for a long time. The colorants are based on direct dyes with different chemical and physical properties and with different coloring and bleaching characteristics. Hence, at least for color shades requiring dye mixtures, it is very difficult to produce uniform decoloration, because the result is determined by the properties of the least active component.

Hence, a need existed for nonoxidative colorants that can be removed at any time without causing major damage to keratin fibers.

SUMMARY OF THE INVENTION

Surprisingly, it has now been found that colorants based on anionic or neutral mono- or polymethine dyes permit outstanding coloring of keratin fibers and that the resulting colorations can again be removed in a simple manner within a short time. Both reducing agents and oxidants are suitable for such decoloration.

Dyes of this type have been known for a long time, and a wide range of substitution patterns can be found in the literature. An overview of these dyes and of their methods of preparation can be found, for example, in Japanese Unexamined Patent Application JP 03-204640. Moreover, many dyes are commercially available.

By means of the colorants of the invention, it is possible to achieve color shades of a modified natural tone, but particularly those in the fashionable range. Moreover, besides the said color shades, it is possible to obtain a number of vivid color highlights, particularly in the yellow to red-violet range. As a result of the high tinting power of the dyes and their high substantivity, the original fiber color can be covered very effectively. As a result, it is possible to satisfy the aforementioned desire to integrate the hair color into fashion and to provide an expression of personality.

Hence, the object of the present application is a colorant for keratin fibers, for example furs, feathers, wool or hair, particularly human hair, characterized in that it contains at least one polymethine dye of formula (I) or a physiologically tolerated salt thereof:

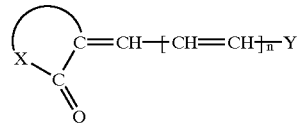

(I)

wherein in general formula (I)

X and the two carbon atoms of the ring system shown in formula (I) together represent the elements needed to form a five-membered or six-membered heterocyclic ring system;

Y denotes an unsubstituted or substituted carbocyclic or heterocyclic aromatic ring containing no hydroxyl group in the α-position to the polymethine group, or a group of general formula (II):

(II)

wherein E1 and E2 denote the radicals of a component with an active methylene group (—CH$_2$—), or a group of general formula (III):

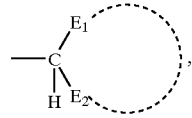

(III)

wherein E1 and E2 denote the radicals of a component with an active methylene group (—CH$_2$—) and together form a nonaromatic ring, and n equals 0, 1 or 2.

For example, the five-membered or six-membered heterocyclic ring in general formula (I) can be a pyrazolone, pyridone, isoxazolone, dioxothiaxoline, rhodanine, dioxoimidazolidine, barbituric acid or thiobarbituric acid group.

In cases where in the general formula (I) substituent Y has general structure (II) or (III), the remaining hydrogen of the aforesaid active methylene component can form tautomers according to the following scheme:

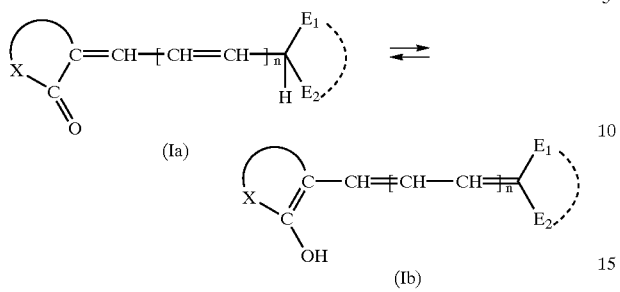

The physiologically tolerated salts of the compounds of formula (I) are, in particular, the pyridinium, tetraalkylphosphonium, tetraarylphosphonium, alkali metal, and ammonium salts, for example the ammonium, triethylammonium, sodium, potassium, N-methylmorpholinium, monoethanolammonium, diethanolammonium and triethanolammonium salts among which the sodium, potassium and particularly ammonium salts are preferred.

Preferred among the compounds of formula (I) are the pyrazolone dyes of general structure (IV):

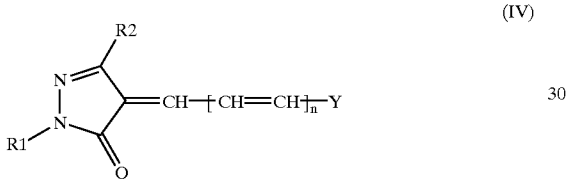

wherein

R1 denotes hydrogen, a straight-chain or branched C1 to C8 alkyl, hydroxyethyl, dihydroxypropyl, methoxyethyl, carboxyethyl or C1 to C4 sulfoalkyl group, a phenyl radical, a phenyl radical substituted with one or more halogen atoms, a phenyl radical substituted with one or two sulfonic acid groups, a phenyl radical substituted with one or two carboxylic acid groups, a phenyl radical substituted with one or more unbranched or branched C1 to C8 alkyl groups, a phenyl radical substituted with one or more unbranched or branched C1 to C8 alkoxy groups, a benzyl radical, a benzyl radical substituted with one or more halogen atoms, a benzyl radical substituted with a C1 to C4 alkyl group, a benzyl radical substituted with a hydroxyl group, a benzyl radical substituted with a methoxy group, a benzyl radical substituted with a carboxyl group, a benzyl radical substituted with a nitro group, a benzyl radical substituted with an amino group or a five-membered or six-membered saturated or unsaturated heterocyclic ring;

R2 denotes hydrogen, a branched or unbranched C1 to C6 alkyl group, a phenyl radical, an amino group, an acylated or sulfonylated amino group, an acetyl, methoxy or carboxylic acid group, a carboxylic acid group esterified with a straight-chain or branched C1 to C8 alcohol or ethylene glycol monomethyl ether or ethylene glycol monoethyl ether, or a carboxamido, carboxanilido or 2-amino-2-oxyethyl group;

Y denotes an aromatic five-membered or six-membered carbocyclic or heterocyclic ring or a benzoanellated aromatic five-membered or six-membered carbocyclic or heterocyclic ring, or Y denotes a radical of general formula (II) or (III), wherein E1 and E2 independently of each other denote a nitrile, alkylsulfonyl, acyl, carboxylic ester or carboxamido group; and n is equal to 0, 1 or 2.

Particularly preferred are pyrazolone dyes of general structure (IV) wherein

R1 denotes a straight-chain or branched C1 to C4 alkyl, hydroxyethyl, dihydroxypropyl, methoxyethyl or C1 to C4 sulfoalkyl group or a phenyl radical or a phenyl radical substituted with one or more halogen atoms, a phenyl radical substituted with one or two sulfonic acid groups or a phenyl radical substituted with one or two carboxylic acid groups;

R2 denotes hydrogen, a methyl or carboxylic acid group or a carboxylic acid group esterified with a straight-chain C1 to C4 alcohol, or a carboxamido group;

Y denotes a donor-substituted phenyl radical, an aromatic five-membered heterocyclic ring or a benzoanellated aromatic five-membered heterocyclic ring; and n equals 0, 1 or 2.

Examples of suitable compounds of formula (IV) are (in all cases written in their acid form):

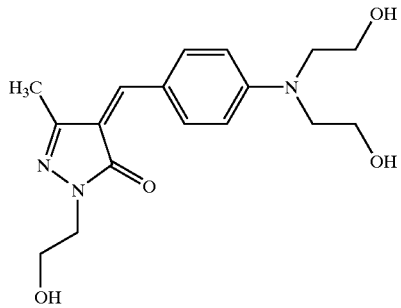

4-(4-(Bis-(2-hydroxyethyl)amino)-benzyliden)-2-(2-hydroxyethyl)-5-methyl-2,4-dihydro-pyrazol-3-one
(1)

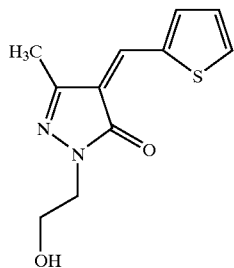

2-(2-Hydroxyethyl)-5-methyl-4-thiophen-2-ylmethylen-2,4-dihydro-pyrazol-3-one (2)

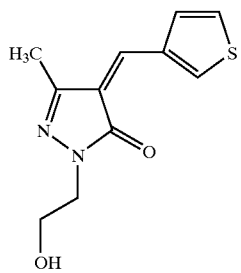

2-(2-hydroxyethyl)-5-methyl-4-thiophen-3-ylmethylen-2,4-dihydro-pyrazol-3-one (3)

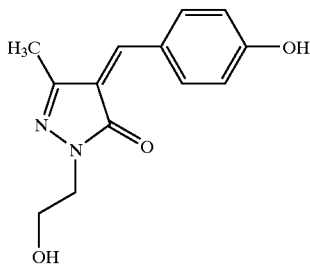

4-(4-Hydroxy-benzyliden)-2-(2-hydroxyethyl)-5-methyl-2,4-dihydro-pyrazol-3-one (4)

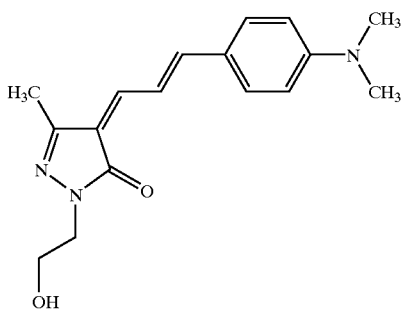

4-(3-(4-Dimethylamino-phenyl)-allyliden)-2-(2-hydroxyethyl)-5-methyl-2,4-dihydro-pyrazol-3-one (5)

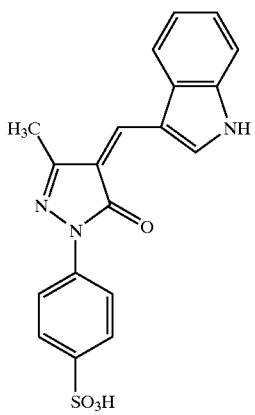

4-(4-(1H-Indol-3-ylmethylen)-3-methyl-5-oxo-4,5-dihydro-pyrazol-1-yl)-benzenesulfonic acid (6)

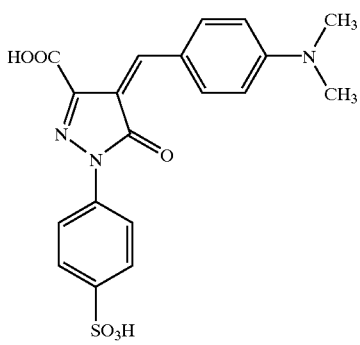

4-(4-Dimethylamino-benzyliden)-5-oxo-1-(4-sulfo-phenyl)-4,5-dihydro-1H-pyrazol-3-carboxylic acid (7)

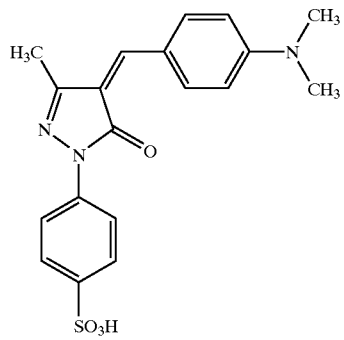

4-(4-(4-Dimethylamino-benzyliden)-3-methyl-5-oxo-4,5-dihydro-pyrazol-1-yl)-benzenesulfonic acid (8)

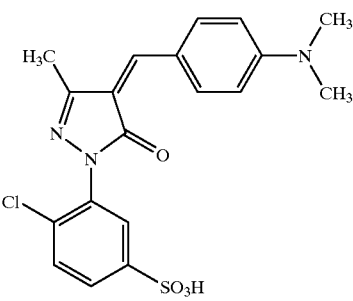

4-Chlor-3-(4-(4-dimethylamino-benzyliden)-3-methyl-5-oxo-4,5-dihydro-pyrazol-1-yl)-benzenesulfonic acid (9)

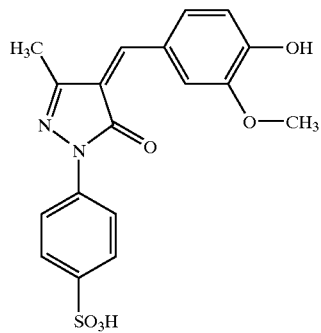

4-(4-(4-Hydroxy-3-methoxy-benzyliden)-3-methyl-5-oxo-4,5-dihydro-pyrazol-1-yl)-benzenesulfonic acid (10)

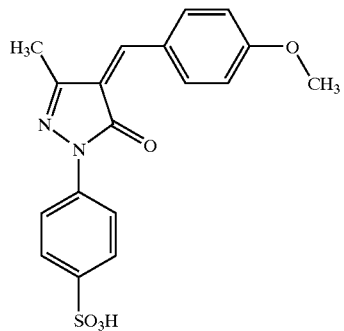

4-(4-(4-Methoxy-benzyliden)-3-methyl-5-oxo-4,5-dihydro-pyrazol-1-yl)-benzenesulfonic acid (11)

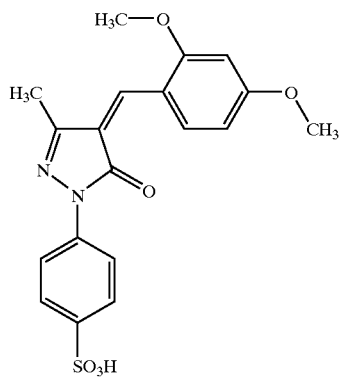

4-(4-(2,4-Dimethoxy-benzyliden)-3-methyl-5-oxo-4,5-dihydro-pyrazol-1-yl)-benzenesulfonic acid (12)

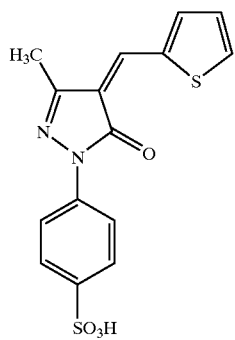

4-(3-Methyl-5-oxo-4-thiophen-2-ylmethylen-4,5-dihydro-pyrazol-1-yl)-benzenesulfonic acid (13)

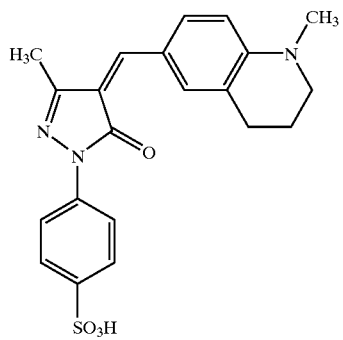

4-(3-Methyl-4-(1-methyl-1,2,3,4-tetrahydro-chinolin-6-ylmethylen)-5-oxo-4,5-dihydro-pyrazol-1-yl)-benzenesulfonic acid (14)

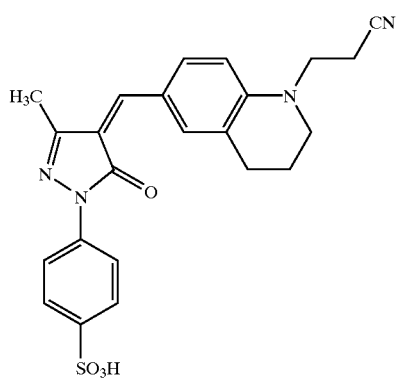

4-(4-(1-(2-Cyan-ethyl)-1,2,3,4-tetrahydro-chinolin-6-ylmethylen)-3-methyl-5-oxo-4,5-dihydro-pyrazol-1-yl)-benzenesulfonic acid (15)

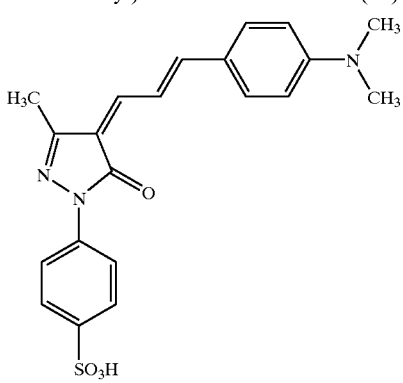

4-(4-(3-(4-Dimethylamino-phenyl)-allyliden)-3-methyl-5-oxo-4,5-dihydro-pyrazol-1-yl)-benzenesulfonic acid (16)

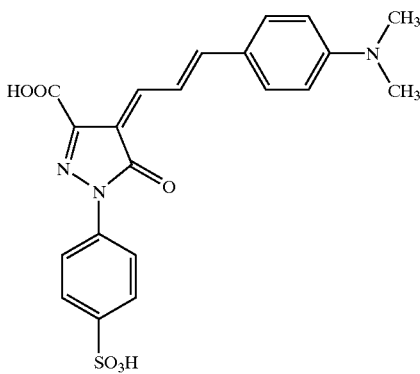

4-(3-(4-Dimethylamino-phenyl)-allyliden)-5-oxo-1-(4-sulfophenyl)-4,5-dihydro-1H-pyrazol-3-carboxylic acid (17)

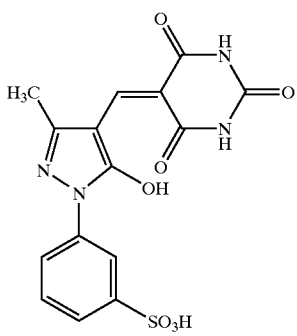

3-(5-Hydroxy-3-methyl-4-(2,4,6-trioxo-tetrahydropyrimidin-5-ylidenmethyl)-pyrazol-1-yl)-benzenesulfonic acid (18)

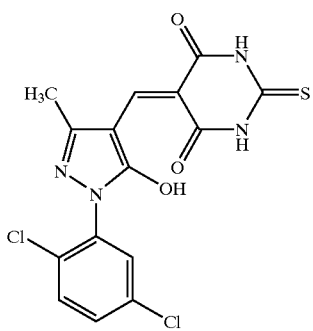

5-(1-(2,5-Dichlorphenyl)-5-hydroxy-3-methyl-1H-pyrazol-4-ylmethylen)-2-thioxo-dihydro-pyrimidin-4,6-dione (19)

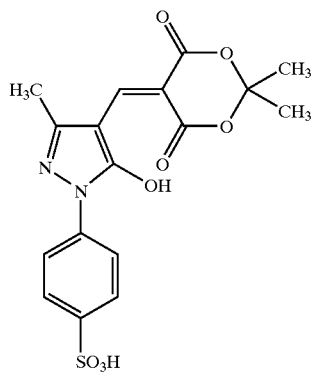

4-(4-(2,2-Dimethyl-4,6-dioxo-[1,3]dioxan-5-ylidenmethyl)-5-hydroxy-3-methyl-pyrazol-1-yl)-benzenesulfonic acid (20)

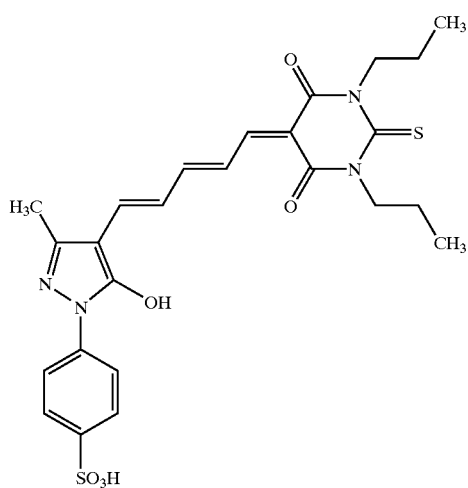

4-(4-(5-(4,6-Dioxo-1,3-dipropyl-2-thioxo-tetrahydro-pyrimidin-5-yliden)-penta-1,3-dienyl)-5-hydroxy-3-methyl-pyrazol-1-yl)-benzenesulfonic acid (21)

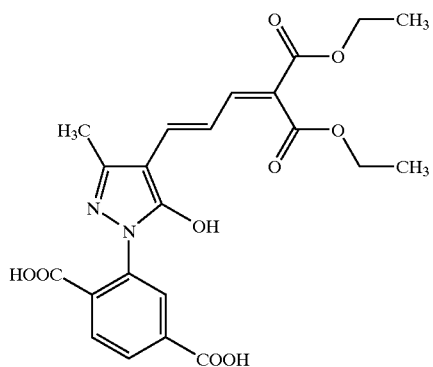

2-(4-(4,4-Bis-ethoxycarbonyl-buta-1,3-dienyl)-5-hydroxy-3-methyl-pyrazol-1-yl)-terephthalic acid (22)

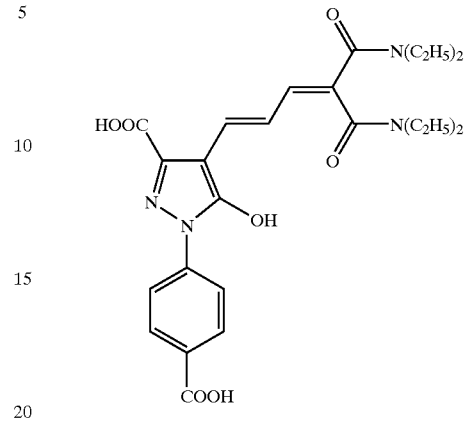

1-(4-Carboxy-phenyl)-4-(4,4-dicarbamoyl-buta-1,3-dienyl)-5-hydroxy-1H-pyrazol-3-carboxylic acid (23)

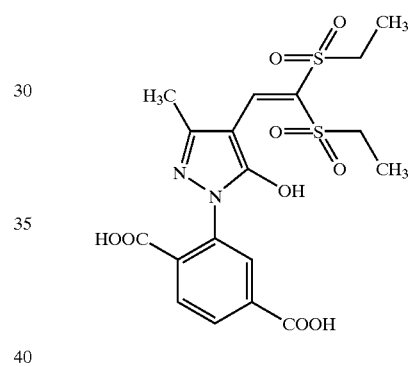

2-(4-(2,2-Bis-ethansulfonyl-vinyl)-5-hydroxy-3-methyl-pyrazol-1-yl)-terephthalic acid (24)

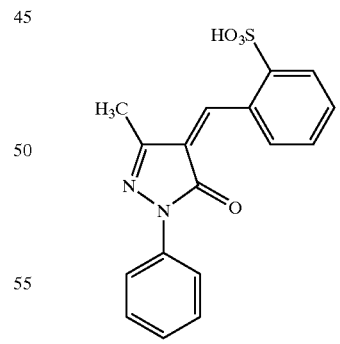

2-(3-Methyl-5-oxo-1-phenyl-1,5-dihydro-pyrazol-4-ylidenemethyl)-benzenesulfonic acid (25)

Particularly well suited are dyes of formula (I) or (IV) which contain sulfonic acid groups and are in the form of their sodium, potassium, ammonium or triethylammonium salts, for example:

11

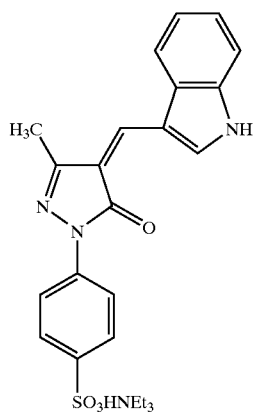

Triethylammonium-4-(4-(1H-indol-3-ylmethylen)-3-
methyl-5-oxo-4,5-dihydro-pyrazol-1-yl)-
benzenesulfonate (6a)

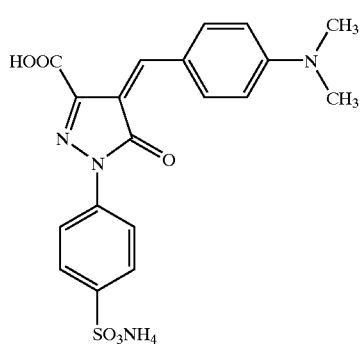

Ammonium-4-(4-dimethylamino-benzyliden)-5-oxo-
1-(4-sulfo-phenyl)-4,5-dihydro-1H-pyrazol-3-
carboxylic acid (7a)

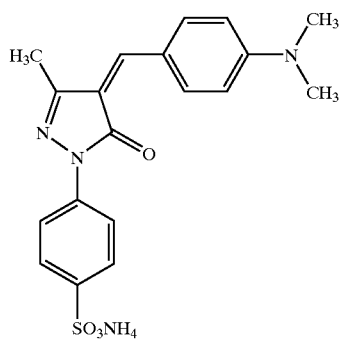

12

Ammonium-4-(4-(4-dimethylamino-benzyliden)-3-
methyl-5-oxo-4,5-dihydro-pyrazol-1-yl)-
benzenesulfonate (8a)

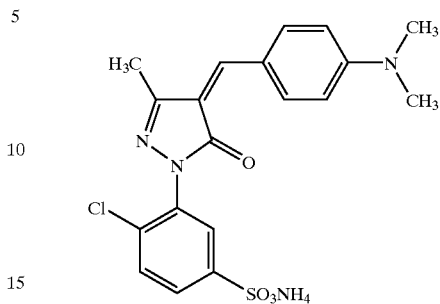

Ammonium-4-chlor-3-(4-(4-dimethylamino-
benzyliden)-3-methyl-5-oxo-4,5-dihydro-pyrazol-1-
yl)-benzenesulfonate (9a)

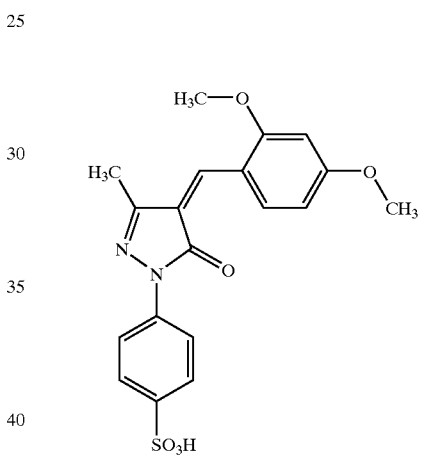

Ammonium-4-(4-(2,4-dimethoxy-benzyliden)-3-
methyl-5-oxo-4,5-dihydro-pyrazol-1-yl)-
benzenesulfonate (12a) [sic-Translator]

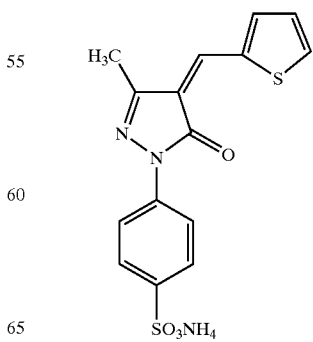

Ammonium-4-(3-methyl-5-oxo-4-thiophen-2-ylmethylen-4,5-dihydro-pyrazol-1-yl)-benzenesulfonate (13a)

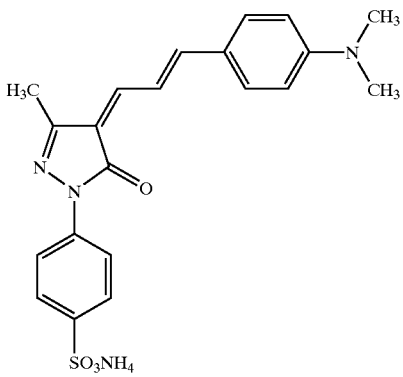

Ammonium-4-(4-(3-(4-dimethylamino-phenyl)-allyliden)-3-methyl-5-oxo-4,5-dihydro-pyrazol-1-yl)-benzenesulfonate (16a)

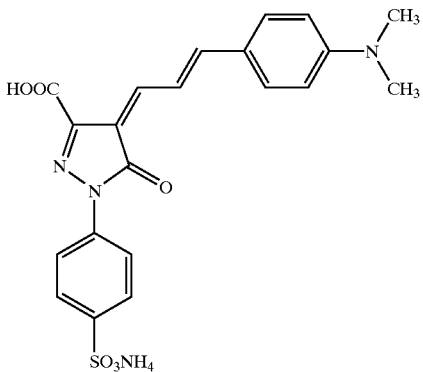

Ammonium-4-(3-(4-dimethylamino-phenyl)-allyliden)-5-oxo-1-(4-sulfophenyl)-4,5-dihydro-1H-pyrazol-3-carboxylic acid (17a)

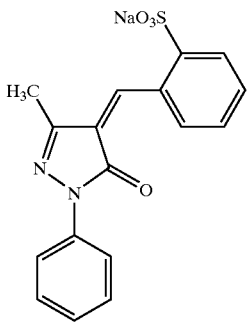

Sodium 2-(3-methyl-5-oxo-1-phenyl-1,5-dihydro-pyrazol-4-ylidenemethyl)-benzenesulfonate (23a)

Combinations of the aforesaid dyes of formula (I) make it possible to obtain uniform coloring from the root to the tip of the hair in a slightly modified natural shade range, and particularly of bright fashionable shades with orange-red highlights. The advantageous properties of the novel dyes manifest themselves particularly on light-damaged and weather-damaged or permanently waved hair.

Although many of the preferred dyes of general structure (IV) have an anionic character and a relatively high molecular weight (which in hair cosmetics is usually a drawback), they show surprisingly good substantivity to hair.

The total amount of polymethine dyes of formula (I) in the hair colorant of the invention is from 0.01 to 5 wt %, preferably about 0.02 to 5 wt % and particularly preferably 0.5 to 4 wt %.

Conventional carriers can be added to the cosmetic systems to increase color intensity. Suitable compounds are, for example, benzyl alcohol, vanillin or isovanillin. Other suitable carriers are described in German Unexamined Patent Application 196 18 595.

The keratin fiber colorant of the invention can be in the form of, for example, a solution, particularly an aqueous-alcoholic solution, or a cream, gel or emulsion. Suitable solvents are, besides water, for example lower aliphatic monohydric or polyhydric alcohols, their esters and ethers or mixtures of said solvents with each other or with water. The maximum boiling point of the aforesaid solvents is about 400° C., a boiling point of 20° to 250° C. being preferred.

It is also possible to dispense said colorant by means of an atomizer or some other suitable pumping device or, in admixture with conventional propellants liquefied under pressure, dispense it from a pressurized container in the form of an aerosol spray or aerosol foam.

The pH of the colorant according to the invention is from 2 to 11, a pH from 2.5 to 8 being particularly preferred. An alkaline pH is preferably obtained with ammonia, but an organic amine, for example monoethanolamine or triethanolamine, can be used in place of ammonia. To obtain an acidic pH, on the other hand, an organic or inorganic acid can be used, for example hydrochloric, sulfuric, phosphoric, ascorbic, glycolic or lactic acid.

Naturally, the aforedescribed colorants can optionally contain other common additives suitable for keratin fiber colorants, for example hair-care agents, wetting agents, thickeners, softeners, preservatives and perfumes as well as other additives listed in the following.

The colorants according to the invention can also contain wetting agents or emulsifiers from the classes of anionic, amphoteric, nonionic or zwitterionic surface-active agents, such as fatty alcohol sulfates, alkanesulfonates, alkylbenzenesulfonates, alkylbetaines, α-olefinsulfonates, ethoxylated fatty alcohols, ethoxylated nonylphenols, fatty alkanolamines, ethoxylated fatty esters, fatty alcohol polyglycol ether sulfates, alkyl polyglucosides, thickeners such as the higher fatty alcohols, starch, alginates, bentonites, cellulose derivatives, vaseline, paraffin oil and fatty acids, water-soluble polymeric thickeners such as various types of natural gum, guar gum, xanthan gum, carob bean flour, pectin, dextran, agar, amylose, amylopectin, dextrins, clays, or fully synthetic hydrocolloids, such as polyvinyl alcohol, furthermore hair-care agents such as lanolin derivatives, cholesterol, pantothenic acid, water-soluble polymers, protein derivatives, provitamins, vitamins, plant extracts, sugar and betaine, auxiliary agents such as humectants, electrolytes, antioxidants, fatty amides, sequestrants, film-forming agents and preservatives.

The aforedescribed colorants can also contain natural or synthetic polymers or modified natural polymers whereby the keratin fiber is strengthened while it is being colored. Such agents are generally referred to as shade or color enhancers. Suitable among the synthetic polymers known to be used in cosmetics for this purpose are, for example, polyvinylpyrrolidone, polyvinyl acetate, polyvinyl alcohol, or polyacrylic compounds, such as polyacrylic acid or polymethacrylic acid, polyacrylonitrile, polyvinyl acetates and copolymers of such compounds, for example polyvinylpyrrolidone-vinyl acetate copolymers. Suitable natural or modified natural polymers are, for example, chitosan, (deacetylated chitin) or chitosan derivatives.

The said constituents are used in amounts that are normal for such purposes. For example, the wetting agents and emulsifiers are used at a concentration of about 0.5 to 30 wt %, the thickeners in an amount from about 0.1 to 25 wt % and the hair-care agents in an amount from about 0.1 to 5 wt %. The aforesaid polymers can be used in the colorants of the invention in amounts that are normal for such colorants, particularly in an amount from about 1 to 5 wt %.

The keratin fiber colorant of the invention is particularly well suited for the coloring of hair. For this purpose, the colorant of the invention is applied to the hair in the usual manner in an amount sufficient for hair coloring, in general in an amount from about 50 to 150 grams. After an exposure time sufficient for hair coloring, usually about 10 to 45 min at 20° to 50° C. and preferably 15 to 30 min at about 40° C., the hair is rinsed with water, optionally washed with a shampoo and/or an aqueous solution of a weak organic acid, for example citric or tartaric acid, again rinsed and then dried.

The colorant with the additional strengthening action is used in the known and conventional manner by wetting the hair with it, styling the hair and then drying.

As regards the range of possible coloring, the hair colorants according to the invention can give rise to a broad spectrum of different shades ranging from natural colors to highly fashionable bright shades, depending on the type and composition of the polymethine dyes used. The advantageous properties of the novel colorants manifest themselves particularly on light-damaged and weather-damaged or permanently waved hair.

The colorants of the invention can additionally contain natural or synthetic direct dyes, for example nitro, azo, quinone, triphenylmethane, basic or acidic dyes. Preferred, however, is the exclusive use of polymethine dyes of formula (I) all of which are mutually compatible because they are structurally related compounds. This is because the exclusive use of polymethine dyes of formula (I) results in highly uniform coloring as well as in very uniform decoloration.

In other words, the exclusive use of polymethine dyes of formula (I) makes it possible to reverse the hair color at any time. In this respect, it is particularly advantageous that the decoloration restores the original pigmentation of the treated hair, it being irrelevant in practice whether the original pigmentation was the natural hair color or was achieved by oxidative hair coloring. It is thus possible to change the natural hair color to a permanent hair color for a desired time period and then, at the end of this period, to restore the natural color in practically unchanged form.

The object of the present application is therefore also a method for temporary coloring of hair ("ON/OFF coloring") whereby uncolored or oxidatively colored hair is tinted with the colorant of the invention in the aforedescribed manner and later (at any time desired by the user) is decolorized with a reducing agent or oxidant.

The color shades obtained with the polymethine dyes of formula (I) can be decolorized completely, for example, reductively by the action of a suitable reducing agent, for example a sulfite, metabisulfite or hydrogen sulfite, for example an alkali metal sulfite, alkali metal hydrogen sulfite or alkali metal metabisulfite (for example sodium sulfite, sodium metabisulfite or potassium metabisulfite), ammonium sulfite or ammonium hydrogen sulfite, or with a suitable oxidant such as, for example, commercial persulfate-containing hair-bleaching powder. Hair-bleaching powders as a rule contain from 5 to 50 wt % and preferably from 15 to 30 wt % of ammonium persulfate or alkali metal persulfate or a mixture of ammonium persulfate and alkali metal persulfate. The decoloration is preferably carried out reductively by use of the aforesaid decolorizing agents (particularly with ammonium sulfite or ammonium hydrogen sulfite), the use of the aforesaid reducing agents in combination with other reducing agents, for example reductones and/or thiols being particularly preferred.

Depending on the color to be decolorized and the temperature (about 20° to 50° C.), the time required for the decolorizing agent to act is from 5 to 45 min and particularly from 5 to 30 minutes. The decolorizing process can be accelerated by heating. At the end of the time of exposure to the decolorizing agent, the hair is rinsed with water, optionally washed with a shampoo and/or treated with a rinse, preferably a neutral or weakly acidic rinse, and then dried. Both the shampoo and the rinse can contain a reductone, for example ascorbic acid.

In this manner, after the decolorization, the original color shade is restored. If, on the other hand, one uses a hair-bleaching agent consisting of a hydrogen peroxide solution, preferably a 6–12% hydrogen peroxide solution, the polymethine dyes of formula (I) are completely decolorized and, in addition, the hair is bleached.

The following examples illustrate the invention in greater detail without limiting the scope of the invention to said examples.

EXAMPLES

Example 1

Method for Preparing 4-(4-(bis-(2-hydroxyethyl) amino)benzylidene)-2-(2-hydroxyethyl)-5-methyl-2, 4-dihydropyrazol-3-one (1)

2.85 g of 5-hydroxy-1-hydroxyethyl-3-methyl-1H-pyrazole and 4-(di-(2-hydroxyethyl)amino)-benzaldehyde in ethanol were allowed to reflux for 4 hours. The reaction mixture was then evaporated, and the residue was caused to crystallize by addition of a small amount of isopropanol.

Yield: 3.3 g of 4-(4-(bis-(2-hydroxyethyl)amino) benzylidene)-2-(2-hydroxyethyl)-5-methyl-2,4-dihydropyrazol-3-one (1)

Melting point: 183–186° C.

$\lambda_{max}$ (H$_2$O)): 466 nm

ε: 39,500

$^1$H-NMR (DMSO): δ=8.55 (d, $^3J_{HH}$=9 Hz, 2H); 7.35 (s, 1H); 685 (d, $^3J_{HH}$=9 Hz, 2H), 4.80 (m, 3H); 3.60 (m, 12H+water); 2.10 ppm (s, 3H).

| | CHN anaylsis: (C$_{17}$H$_{23}$N$_3$O$_4$) | | |
|---|---|---|---|
| | C | H | N |
| Calcd. | 61.25 | 6.95 | 12.60 |
| Found | 61.23 | 7.01 | 12.51 |

Example 2

Method for Preparing 2-(2-hydroxyethyl)-5-methyl-4-thiophen-2-ylmethylene-2,4-dihydropyrazol-3-one (2)

2.85 g of 5-hydroxy-1-hydroxyethyl-3-methyl-1H-pyrazole and 2.25 g of thiophene-2-carboxaldehyde in 30 mL of 2-butanol were allowed to reflux for 7 hours. Upon cooling, a vivid orange-colored dye crystallized.

Yield: 2.0 g of 2-(2-hydroxyethyl)-5-methyl-4-thiophen-2-ylmethylene-2,4-dihydropyrazol-3-one (2)

Melting point: 142–144° C.

$\lambda_{max}$ (methanol): 349 nm, $\epsilon$=21,600

| CHNS analysis: ($C_{11}H_{12}N_2O_2S$) | | | | |
|---|---|---|---|---|
| | C | H | N | S |
| Calcd. | 55.91 | 5.12 | 11.86 | 13.57 |
| Found | 56.19 | 5.08 | 12.00 | 13.78 |

Example 3

Method for Preparing 4-(4-hydroxybenzylidene)-2-(2-hydroxyethyl)-5-methyl-2,4-dihydropyrazol-3-one (4)

2.85 g of 5-hydroxy-1-hydroxyethyl-3-methyl-1H-pyrazole and 2.45 g of 4-hydroxybenzaldehyde in 30 mL of 2-butanol were allowed to reflux. After 16 h, the reaction mixture was cooled, then poured onto 100 mL of glacial acetic acid and filtered. This gave 3.3 g of a by-product, probably the acetal of the following formula:

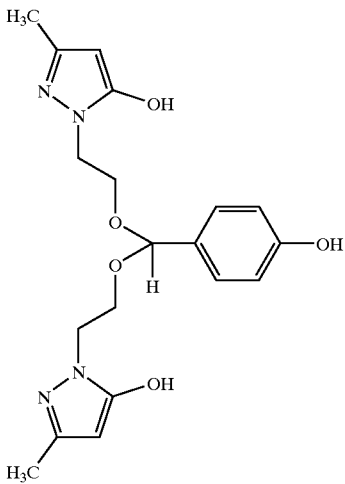

(melting point: 197–200° C.; $^1$H-NMR (DMSO); δ=6.95 (d, $^3J_{HH}$=7.5 Hz, 2H), 6.65 (d, $^3J_{HH}$=7.5 Hz, 2H), 4.6 (s, 1H), 3.75 (m, 4H), 4.60 (m, 4H), 2.1 ppm (s, 6H).

The mother liquor was evaporated, and the residue was caused to crystallize by addition of isopropanol.

Yield: 1.6 g of 4-(4-hydroxybenzylidene)-2-(2-hydroxyethyl)-5-methyl-2,4-dihydro-pyrazol-3-one (4) (vivid orange-colored crystals).

Melting point: 207–210° C.

$^1$H-NMR (DMSO): δ=8.6 (d, $^3J_{HH}$=9 Hz, 2H), 7.4 (s, 1H), 6.9 (d, $^3J_{HH}$=9 Hz, 2H), 3.65 (m, 4H), 2.15 ppm (s, 3H).

Example 4

Method for Preparing 4-(3-(4-dimethylaminophenyl)allylidene)-2-(2-hydroxyethyl)-5-methyl-2,4-dihydropyrazol-3-one (5)

12.85 g of 5-hydroxy-1-hydroxyethyl-3-methyl-1H-pyrazole and 3.5 g of 4-dimethylaminocinnamaldehyde in 30 mL of 2-butanol were allowed to reflux 14 hours. Upon cooling, the dye crystallized.

Yield: 1.9 g of 4-(3-(4-dimethylaminophenyl)allylidene)-2-(2-hydroxyethyl)-5-methyl-2,4-dihydropyrazol-3-one (5)

Melting point: 122° C.

$\lambda_{max}$ (methanol): 510 nm $\epsilon$: 17,600

Example 5

Method for Preparing Triethylammonium 4-(4-(1H-indol-3-ylmethylene)-3-methyl-5-oxo-4,5-dihydropyrazol-1-yl)benzenesulfonate (6a)

2.55 g of 5-hydroxy-3-methyl-1-(4-sulfophenyl)-1H-pyrazole, 1.45 g of indole-3-carboxaldehyde and 1.05 g of triethylamine in 25 mL of ethanol were heated at 60° C. After 12 hours, the mixture was cooled, acetone was added dropwise so as to induce crystallization, and the mixture was then filtered.

Yield: 2.1 g triethylammonium 4-(4-(1H-indol-3-ylmethylene)-3-methyl-5-oxo-4,5-dihydropyrazol-1-yl)benzenesulfonate (6a) (red-brown product)

Melting point: >250° C.

$\lambda_{max}$ ($H_2O$): 406 nm $\epsilon$: 29,500

| CHNS analysis: ($C_{19}H_{15}N_3O_4S \times C_6H_{16}N \times 0.5H_2O$) | | | | |
|---|---|---|---|---|
| Calcd. | 61.05 | 6.36 | 11.40 | 6.52 |
| Found | 61.43 | 6.29 | 11.41 | 6.67 |

Example 6

Method for Preparing Ammonium 4-(4-dimethylaminobenzylidene)-5-oxo-1-(4-sulfophenyl)-4,5-dihydro-1H-pyrazole-3-carboxylic acid (7a)

2.85 g of 5-hydroxy-1-(4-sulfophenyl)-1H-pyrazole-3-carboxylic acid, 1.65 g of 4-dimethylaminobenzaldehyde and 0.8 g of ammonium acetate in 25 mL of ethanol were heated at 60° C. After 7 hours, the mixture was cooled and filtered.

Yield: 3.9 g of ammonium 4-(4-dimethylaminobenzylidene)-5-oxo-1-(4-sulfophenyl)-4,5-dihydro-1H-pyrazole-3-carboxylic acid (7a) (orange-red product)

Melting point: >250° C.

$\lambda_{max}$ (methanol): 482 nm $\epsilon$: 39,000

$^1$H-NMR ($D_2O$): δ=7.9–7.5 (m, 8H); 6.0 (d, 1H); 2.30 ppm (s, 6H).

Example 7

Method for Preparing Ammonium-4-(4-(2,4-dimethoxybenzylidene)-3-methyl-5-oxo-4,5-dihydropyrazol-1-yl)benzenesulfonate (12a)

2.55 g of 5-hydroxy-3-methyl-1-(4-sulfophenyl)-1H-pyrazole, 1.83 g 2,4-dimethoxybenzaldehyde and 0.8 g of ammonium acetate in 25 mL of ethanol were heated at 70° C. After 5 hours, the mixture was cooled and filtered.

Yield: 4.2 g of ammonium-4-(4-(2,4-dimethoxy-benzylidene)-3-methyl-5-oxo-4,5-dihydropyrazol-1-yl)benzenesulfonate (12a) (orange-red product)

Melting point: >250° C.

$^1$H-NMR (DMSO): δ=9.6 (d, $^3J_{HH}$=10 Hz, 1H); (d, $^3J_{HH}$=9 Hz, 2H); 7.85 (s, 1H); 7.7 (d, $^3J_{HH}$=9 Hz, 2H); 7.2 (s, 4H); 6.65 (m, 2H); 3.9 (s, 3H); 3.85 (s, 3H); 2.25 (s, 3H).

Example 8

Method for Preparing Ammonium 4-(3-methyl-5-oxo-4-thiophen-2-ylmethylene-4,5-dihydropyrazol-1-yl)benzenesulfonate (13a)

12.75 g of 5-hydroxy-3-methyl-1-(4-sulfophenyl)-1H-pyrazole, 6.2 g of thiophene-2-carboxaldehyde and 3.85 g of ammonium acetate in 100 mL of ethanol were heated at 80° C. After 4 hours, the mixture was cooled and filtered. The crude product was allowed to reflux in 250 mL of methanol for 30 min and the mixture was then cooled and filtered.

Yield: 15.6 g of ammonium 4-(3-methyl-5-oxo-4-thiophen-2-ylmethylene-4,5-dihydropyrazol-1-yl)benzenesulfonate (13a) (orange-colored product)

Melting point: >250° C.

$λ_{max}$ (methanol): 360 nm

ε: 66,800

$^1$H-NMR (DMSO): δ=8.35 (s, 1H); 8.25 (d, $^3J_{HH}$=8.25 Hz, 2H); 8.05 (d, $^3J_{HH}$=8 Hz, 2H); 7.80 (d, $^3J_{HH}$=8 Hz, 2H); 7.40 (m, 5H); 2.35 ppm (s, 3H).

Example 9

Method for Preparing Sodium 2-(3-methyl-5-oxo-1-phenyl-1,5-dihydropyrazol-4-ylidenemethyl)benzenesulfonate (25a)

2.1 g of sodium benzaldehyde-2-sulfonate, 1.75 g of 3-methyl-1-phenyl-2-pyrazolin-5-one and 1 g of triethylamine in 20 mL of ethanol were allowed to reflux 5 hours. After cooling to room temperature, the precipitate was filtered off and dried.

Yield: 0.5 g of sodium 2-(3-methyl-5-oxo-1-phenyl-1,5-dihydropyrazol-4-ylidenemethyl)benzenesulfonate (25a) (red-brown powder)

Melting point: >250° C.

$λ_{max}$ (H$_2$O): 361 nm

ε: 17,600

$^1$H-NMR (90 MHz, D$_2$O): δ=8.7–7.0 (m, 10H); 2.3 ppm (s, 3H).

Example 10
Colorant

| | |
|---|---|
| 10.0 g | of ethanol |
| 10.0 g | of polyoxyethylene lauryl ether (25% aqueous solution) |
| 0.8 g | of 4-(4-(bis-(2-hydroxyethylamino)benzylidene-2-(2-hydroxyethyl)-5-methyl-2,4-dihydropyrazol-3-one (1) |
| to 100.0 g | water, demineralized |

The colorant solution was applied to bleached hair. After an exposure time of 20 min at 40° C., the hair was washed with water and dried. The hair color was of a vivid orange shade.

For decolorization, the hair was then treated with an aqueous solution of the reducing agent indicated in the following table. Decolorization occurred within a few minutes. The hair was thoroughly rinsed with water and then dried. The decolorized hair was nearly white.

| | L* | a* | b* | ΔE$_{1/2}$ | Decolorization, % |
|---|---|---|---|---|---|
| Untreated hair | 84,80 | −0,75 | 11,53 | | |
| Colored hair | 60,13 | 48,54 | 70,96 | 81,06 | |
| Hair decol. with 10% Na$_2$SO$_3$ | 80,36 | 0,07 | 15,41 | 76,45 | 94 |

Example 11
Colorant

| | |
|---|---|
| 10.0 g | of ethanol |
| 10.0 g | of polyoxyethylene lauryl ether (25% aqueous solution) |
| 0.6 g | of 4-(4-hydroxybenzylidene)-2-(2-hydroxyethyl)-5-methyl-2,4-dihydropyrazol-3-one (4) |
| to 100.0 g | water, demineralized |

The colorant solution was applied to bleached hair. After an exposure time of 20 min at 40° C., the hair was washed with water and dried. The hair color was of a lemon-yellow shade.

For decolorization, the hair was then treated with an aqueous solution of the reducing agent indicated in the following table. Decolorization occurred within a few minutes. The hair was thoroughly rinsed with water and then dried. The decolorized hair was white.

| | L* | a* | b* | ΔE$_{1/2}$ | Decolorization, % |
|---|---|---|---|---|---|
| Untreated hair | 84,80 | −0,75 | 11,53 | | |
| Colored hair | 77,86 | 6,81 | 80,21 | 69,44 | |
| Hair decol. with 10% Na$_2$SO$_3$ | 82,98 | 0,69 | 11,54 | 69,13 | 100 |

Example 12
Colorant

| | |
|---|---|
| 5.0 g | of ethanol |
| 1.5 g | of glycolic acid |
| 2.0 g | of sodium cocoamphoacetate (50% aqueous solution) |
| 5.0 g | of benzyl alcohol |
| 1.1 g | of ammonium 4-(4-dimethylaminobenzylidene)-5-oxo-1-(4-sulfophenyl)-4,5-dihydro-1H-pyrazole-3-carboxylic acid (7a) |
| to 100.0 g | water, demineralized |

The colorant solution was applied to bleached hair. After an exposure time of 20 min at 40° C., the hair was washed with water and dried. The hair color was of a vivid orange-red shade.

For decolorization, the hair was treated with an aqueous solution of the reducing agent indicated in the following table. Decolorization occurred within a few minutes. The hair was thoroughly rinsed with water and then dried. The decolorized hair retained bright beige highlights.

|  | L* | a* | b* | $\Delta E_{1/2}$ | Decoloriza-tion, % |
|---|---|---|---|---|---|
| Untreated hair | 84,80 | −0,75 | 11,53 | | |
| Colored hair | 45,58 | 64,70 | 45,45 | 83,50 | |
| Hair decol. with 10% Na₂SO₃ | 83,36 | 7,56 | 17,28 | 74,07 | 89 |

Example 13

Colorant

The hair colored as in the preceding example was treated with a solution containing 5% of sodium sulfite and 5% of ascorbic acid at 20° C. for 8 minutes. The hair became definitely lighter than the hair decolored as in Example 11.

|  | L* | a* | b* | $\Delta E_{1/2}$ | Decoloriza-tion, % |
|---|---|---|---|---|---|
| Untreated hair | 84,80 | −0,75 | 11,53 | | |
| Colored hair | 45,58 | 64,70 | 45,45 | 83,50 | |
| Hair decol. with 5% Na₂SO₃/5% ascorbic acid | 85,07 | 3,08 | 16,98 | 78,53 | 94 |

Example 14

Colorant

| 5.0 g | of ethanol |
|---|---|
| 1 5 g | of glycolic acid |
| 2.0 g | of sodium cocoamphoacetate (50% aqueous solution) |
| 5.0 g | of benzyl alcohol |
| 1.0 g | of ammonium-4-(4-(2,4-dimethoxybenzylidene)-3-methyl-5-oxo-4,5-dihydropyrazol-1-yl)benzenesulfonate (12a) |
| to 100.0 g | water, demineralized |

The colorant solution was applied to bleached hair. After an exposure time of 20 min at 40° C., the hair was washed with water and dried. The hair color had a vivid yellow-orange shade.

For decolorization, the hair was treated with an aqueous solution of the reducing agent indicated in the following table. Decolorization occurred within a few minutes. The hair was thoroughly rinsed with water and then dried. The decolorized hair was white.

|  | L* | a* | b* | $\Delta E_{1/2}$ | Decolorization, % |
|---|---|---|---|---|---|
| Untreated hair | 84.80 | −0.75 | 11.53 | | |
| Colored hair | 70.34 | 27.18 | 82.45 | 77.58 | |
| Hair decol. with 10% Na₂SO₃ | 86.80 | −1.31 | 13.95 | 75.99 | 98 |

Example 15

Colorant

| 5.0 g | of ethanol |
|---|---|
| 1.5 g | of glycolic acid |
| 2.0 g | of sodium cocoamphoacetate (50% aqueous solution) |
| 5.0 g | of benzyl alcohol |
| 1.0 g | of ammonium 4-(3-methyl-5-oxo-4-thiophen-2-ylmethylene-4,5-dihydropyrazol-1-yl)benzenesulfonate (13a) |
| to 100.0 g | water, demineralized |

The colorant solution was applied to bleached hair. After an exposure time of 20 min at 40° C., the hair was washed with water and dried. The hair color had a golden yellow shade.

For decolorization, the hair was then treated with an aqueous solution of the reducing agent indicated in the following table. Decolorization occurred within a few minutes. The hair was thoroughly rinsed with water and then dried. The hair was white.

|  | L* | a* | b* | $\Delta E_{1/2}$ | Decolorization, % |
|---|---|---|---|---|---|
| Untreated hair | 84.80 | −0.75 | 11.53 | | |
| Colored hair | 67.65 | 32.34 | 69.30 | 68.75 | |
| Hair decol. with 10% Na₂SO₃ | 85.80 | −1.15 | 15.79 | 65.68 | 96 |

Example 16

Colorant

| 5.0 g | of ethanol |
|---|---|
| 1.5 g | of glycolic acid |
| 2.0 g | of sodium cocoamphoacetate (50% aqueous solution) |
| 5.0 g | of benzyl alcohol |
| 0.8 g | of ammonium 4-(4-(3-(4-dimethylaminophenyl)allylidene)-3-methyl-5-oxo-4,5-dihydropyrazol-1-yl)benzenesulfonate (16a) |
| to 100.0 g | water, demineralized |

The colorant solution was applied to bleached hair. After an exposure time of 20 min at 40° C., the hair was washed with water and dried. The hair color had a wine-red shade.

For decolorization, the hair was treated with an aqueous solution of the reducing agent indicated in the following table. Decolorization occurred within a few minutes. The hair was thoroughly rinsed with water and then dried. The decolorized hair retained pink highlights.

|  | L* | a* | b* | $\Delta E_{1/2}$ | Decolorization, % |
|---|---|---|---|---|---|
| Untreated hair | 84.80 | −0.75 | 11.53 | | |
| Colored hair | 18.64 | 16.61 | −0.55 | 69.46 | |
| Hair decol. with 10% Na₂SO₃ | 73.74 | 11.75 | 3.99 | 55.50 | 80 |

Example 17

Colorant

| | |
|---|---|
| 5.0 g | of ethanol |
| 1.5 g | of glycolic acid |
| 2.0 g | of sodium cocoamphoacetate (50% aqueous solution) |
| 5.0 g | of benzyl alcohol |
| 0.9 g | of sodium 2-(3-methyl-5-oxo-1-phenyl-1,5-dihydropyrazol-4-ylidene-methyl)benzenesulfonate (25a) |
| to 100.0 g | water, demineralized |

The colorant solution was applied to bleached hair. After an exposure time of 20 min at 40° C., the hair was washed with water and dried. The hair color had a fawn shade.

For decolorization, the hair was treated with an aqueous solution of the reducing agent indicated in the following table. Decolorization occurred within a few minutes. The hair was thoroughly rinsed with water and then dried. The decolorized hair was bright beige.

| | L* | a* | b* | $\Delta E_{1/2}$ | Decolorization, % |
|---|---|---|---|---|---|
| Untreated hair | 84.80 | −0.75 | 11.53 | | |
| Colored hair | 47.02 | 42.51 | 35.69 | 62.31 | |
| Hair decol. with 10% Na$_2$SO$_3$ | 81.95 | 5.73 | 19.23 | 53.33 | 86 |

Example 18

Colorant

| | |
|---|---|
| 5.0 g | of ethanol |
| 1.5 g | of glycolic acid |
| 2.0 g | of sodium cocoamphoacetate (50% aqueous solution) |
| 5.0 g | of benzyl alcohol |
| 1.1 g | of ammonium 4-chloro-3-(4-(4-dimethylaminobenzylidene)-3-methyl-5-oxo-4,5-dihydropyrazol-1-yl)benzenesulfonate (9a) |
| to 100.0 g | water, demineralized |

The colorant solution was applied to medium-blond hair. After an exposure time of 20 min at 40° C., the hair was washed with water and dried. The hair color was of a copper shade.

For decolorization, the hair was treated with an aqueous solution of the decolorizing agent indicated in the following table. Decolorization occurred within a few minutes. The hair was thoroughly rinsed with water and then dried.

| | L* | a* | b* | $\Delta E_{1/2}$ | Decolorization, % |
|---|---|---|---|---|---|
| Untreated hair | 36.18 | 7.89 | 14.25 | | |
| Colored hair | 30.21 | 19.12 | 19.76 | 13.86 | |
| Hair treated with 5% Na$_2$SO$_3$ 5% ascorbic acid | 35.33 | 8.90 | 15.86 | 12.08 | 87 |
| Oxidatively treated hair (mixture of 45% K persulfate + 6% NH$_4$ persulfate/water, 1:1) | 36.64 | 9.96 | 17.33 | 11.45 | 83 |

| | L* | a* | b* | $\Delta E_{1/2}$ | Decolorization, % |
|---|---|---|---|---|---|
| Bleached hair (mixture of 45% potassium persulfate + 6% ammonium persulfate + 6% hydrogen peroxide, 1:1) | 62.44 | 10.02 | 30.00 | 35.02 | 253*) |

Example 19

Color Change on Oxidatively Colored Hair

Bleached hair that had been colored medium-blond with a commercial oxidative colorant was treated with the colorant of Example 17. After an exposure time of 20 min at 40° C, the hair was washed with water and dried. The hair color had a medium copper shade.

For decolorization, the hair was treated as indicated in the following table. After a few minutes, the shade of the precolored hair was restored, with additional brightening. Because, in addition, the oxidative dye underwent a marked color change, a calculation of the degree of decolorization did not make sense.

| | L* | a* | b* | Shade |
|---|---|---|---|---|
| Oxidatively colored hair | 37.24 | 4.76 | 12.78 | medium-blond |
| Hair colored as per Ex. 18 | 28.77 | 23.94 | 17.42 | copper |
| Oxidatively colored hair (mixt. of 45% K persulfate + 6% NH$_4$ persulfate/water, 1:1) | 44.45 | 14.91 | 23.65 | similar to that of oxidatively colored hair |
| Bleached hair (mixt. of 45% K persulfate + 6% NH$_4$ persulfate/6% H$_2$O$_2$, 1:1) | 77.69 | 5.64 | 20.72 | light-blond |
| Hair treated with 5% Na$_2$SO$_3$/5% ascorbic acid | 46.53 | 7.81 | 21.65 | similar to reference shade |

Example 20

Colorant with Carrier

| | |
|---|---|
| 5.0 g | of ethanol |
| 2.0 g | of lactic acid |
| 2.0 g | of sodium cocoamphoacetate (50% aqueous solution) |
| 5.0 g | of carrier as indicated in the following table |
| 1.0 g | of ammonium 4-(4-dimethylaminobenzylidene)-5-oxo-1-(4-sulfophenyl)-4,5-dihydro-1H-pyrazole-3-carboxylic acid (7a) |
| to 100.0 g | water, demineralized |

The colorant solution was applied to bleached hair. After an exposure time of 20 min at 40° C., the hair was washed with water and dried. The colorant devoid of carrier gave a bright orange shade whereas the colorants containing the carrier gave intense orange-red shades.

| Example | Carrier | L* | a* | b* |
|---|---|---|---|---|
| a | — | 61,94 | 42,19 | 44,18 |
| b | Isovanillin | 47,70 | 65,56 | 48,05 |
| c | 2-Hydroxymethylthiophene | 46,51 | 65,71 | 47,71 |
| d | Benzyl alcohol | 45,58 | 64,70 | 45,45 |

The L*a*b* color values given in the preceding examples were measured with a Minolta Chromameter II color-measuring instrument.

The L-value indicates the brightness (in other words, the lower the L value, the higher is the color intensity). The a-value is a measure of the red content (namely, the higher the a-value the higher is the red content). The b-value is a measure of the blue content of the color, the blue content being the higher the more negative is the b-value.

The value of ΔE indicates the difference in color between the untreated and the colored hair or between the colored and the decolorized hair. It is determined as follows:

$$\Delta E = \sqrt{(L_i - L_0)^2 + (a_i - a_0)^2 + (b_i - b_0)^2}$$

where $L_0$, $a_0$ and $b_0$ are the values measured before coloring or before decolorizing, $L_1$, $a_1$, and $b_1$ are the values after coloring and $L_2$, $a_2$ and $b_2$ the values after decolorization.

The percentage decolorization was determined according to the following expression:

$$\text{Decolorization}, \% = (\Delta E_2 / \Delta E_1) \times 100$$

Here, $\Delta E_1$ refers to the coloring step and $\Delta E_2$ to the decolorizing step.

The calculation can only serve as confirmation of the visual impression, because ΔE indicates only the color difference and not the direction of the change.

Unless otherwise indicated, all percentages given in the present application are by weight.

What is claimed is:

1. A colorant for keratin fibers, said colorant containing water, from 0.5 to 30 percent by weight of at least one surfactant member selected from the group consisting of anionic surface-active compounds, cationic surface-active compounds, nonionic surface-active compounds and amphoteric surface-active compounds and from 0.01 to 5 percent by weight of at least one dye compound of formula (IV), or a physiologically tolerated salt thereof;

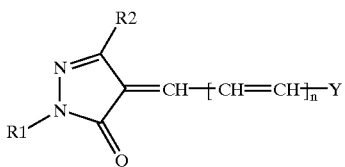

(IV)

wherein

R1 represents hydrogen, a straight-chain or branched alkyl group containing one to eight carbon atoms, a hydroxyethyl group, a dihydroxypropyl group, a methoxyethyl group, a carboxy ethyl group, a sulfoalkyl group containing one to four carbon atoms, a phenyl radical, a phenyl radical substituted with at least one halogen atom, a phenyl radical substituted with one or two sulfonic acid groups, a phenyl radical substituted with at least one carboxylic acid group, a phenyl radical substituted with at least one straight-chain or branched alkyl group having one to eight carbon atoms, a phenyl radical substituted with at least one straight-chain or branched alkoxy group having one to eight carbon atoms, a benzyl radical, a benzyl radical substituted with at least one halogen atom, a benzyl radical substituted with an alkyl group having one to four carbon atoms, a benzyl radical substituted with a hydroxyl group, a benzyl radical substituted with a methoxy group, a benzyl radical substituted with a carboxyl group, a benzyl radical substituted with a nitro group, a benzyl radical substituted with an amino group or a five-membered or six-membered heterocyclic ring;

R2 represents hydrogen, a branched or straight-chain alkyl group having one to six carbon atoms, a phenyl radical, an amino group, an acylated amino group, a sulfonylated amino group, an acetyl group, a methoxy group, a carboxylic acid group, a carboxylic acid group esterified with a straight-chain or branched alcohol having one to eight carbon atoms, a carboxylic acid group esterified with ethylene glycol monomethyl ether, a carboxylic acid group esterified with ethylene glycol monoethyl ether, a carboxamido group, a carboxanilido group or a 2-amino-2-oxyethyl group; and Y represents an aromatic five-membered or six-membered carbocyclic or heterocyclic ring or a benzoanellated aromatic five-membered or six membered carbocyclic or heterocyclic ring, with no hydroxy group at an α position on said ring, or Y represents a radical of the formula (II) or (III):

(II)

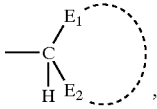

(III)

wherein E1 and E2, independently of each other, each represent a nitrile group, an alkylsulfonyl group, acyl group, a carboxylate ester group or a carboxamido group; and n is 0, 1 or 2.

2. The colorant as defined in claim 1, wherein said R1 represents said straight-chain or branched alkyl group containing one to eight carbon atoms, said hydroxyethyl group, said dihydroxypropyl group, said methoxyethyl group, said carboxy ethyl group, said sulfoalkyl group containing one to four carbon atoms, said phenyl radical, said phenyl radical substituted with at least one halogen atom, said phenyl radical substituted with one or two sulfonic acid groups or said phenyl radical substituted with at least one carboxylic acid group; said R2 represents said hydrogen, a methyl group, said carboxylic acid group, a carboxylic acid group esterified with a straight-chain or branched alcohol with one to four carbon atoms, or said carboxamido group; and said Y represents said aromatic five-membered heterocyclic ring or said benzoanellated aromatic five-membered heterocyclic ring.

3. The colorant as defined in claim 2, wherein said R1 represents one of said alkyl groups having from one to four carbon atoms.

4. The colorant as defined in claim 1, wherein said physiologically tolerated salt is selected from the group consisting of pyridinium, tetraalkylphosphonium, tetraarylphosphonium, ammonium, triethylammonium, sodium, potassium, N-methylmorpholinium, monoethanolammonium, diethanolammonium and triethanolammonium salts of said at least one dye compound of the formula (IV).

5. The colorant as defined in claim 1, having a pH of from 2 to 11.

6. The colorant as defined in claim 1, further comprising a carrier.

7. The colorant as defined in claim 1, further comprising at least one polymer ingredient selected from the group consisting of natural polymers, synthetic polymers and modified polymers of natural origin.

8. A colorant for keratin fibers, said colorant comprising water, from 0.5 to 30 percent by weight of at least one surfactant member selected from the group consisting of anionic surface-active compounds, cationic surface-active compounds, nonionic surface-active compounds and amphoteric surface-active compounds and from 0.01 to 5 percent by weight of at least one dye compound selected from the group consisting of 4-4(bis-(2-hydroxyethyl)-amino)benzylidene)-2-(2-hydroxy-ethyl)-5-methyl-2,4-dihydropyrazol-3-one;2-(2-hydroxyethyl)-5-methyl-4-thiophen-2-yl-methylene-2,4-dihydropyrazol-3-one; 2-(2-hydroxyethyl)-5-methyl-4-thiophen-3-yl-methylene-2,4-dihydropyrazol-3-one; 4-(4-hydroxybenzylidene)-2-(2-hydroxy-ethyl)-5-methyl-2,4-dihydropyrazol-3-one, 4-(3-(4-dimethylaminophenyl)-allylidene)-2-(2-hydroxyethyl)-5-methyl-2,4-dihydropyrazol-3-one; 4-(4-(1H-indol-3-ylmethylene) 3-methyl-5-oxo-4,5-dihydropyrazol-1-yl) benzene sulfonic acid; triethylammonium-4-(4-(1H-indol-3-ylmethylene)-3-methyl-5-oxo-4,5-dihydropyrazol-1-yl) benzene sulfonate; 4-(4-dimethylaminobenzylidene)-5-oxo-1-(4-sulfophenyl)-4,5-dihydro-1H-pyrazole-3-carboxylic acid; ammonium 4-(4-dimethyl-aminobenzylidene)-5-oxo-1-(4-sulfophenyl)-4,5-dihydro-1H-pyrazole-3-carboxylic acid; 4-(4-(4-dimethylaminobenzylidene)-3-methyl-5-oxo-4,5-dihydropyrazol-1-yl)benzene sulfonic acid; ammonium 4-(4-(4-dimethylamino-benzylidene)-3-methyl-5-oxo-4,5-dihydropyrazol-1-yl)benzene sulfonate; 4-chloro-3-(4-(4-dimethylaminobenzylidene)-3-methyl-5-oxo-4,5-dihydropyrazol-1-yl)benzene sulfonic acid; ammonium 4-chloro-3-(4-(4-dimethylamino-benzylidene)-3-methyl-5-oxo-4,5-dihydropyrazol-1-yl)benzene sulfonate; 4-(4-(4-hydroxy-3-methoxybenzylidene)-3-methyl-5-oxo-4,5-dihydropyrazol-1-yl)benzene sulfonic acid; 4-(4-(4-methoxybenzylidene)-3-methyl-5-oxo-4,5-dihydropyrazol-1-yl)benzene sulfonic acid; 4-(4-(2,4-dimethoxy-benzylidene)-3-methyl-5-oxo-4,5-dihydropyrazol-1-yl) benzene sulfonic acid; ammonium 4-(4-(2,4-dimethoxybenzylidene)-3-methyl-5-oxo-4,5-dihydropyrazol-1-yl)benzene sulfonate; 4-(3-methyl-5-oxo-4-thiophen-2-ylmethylene-4,5-dihydropyrazol-1-yl) benzene sulfonic acid; ammonium 4-(3-methyl-5-oxo-4-thiophen-2-ylmethylene-4,5-dihydropyrazol-1-yl)benzene sulfonate; 4-(3-methyl-4-(1-methyl-1,2,3,4-tetrahydroquinolin-6-ylmethylene)-5-oxo-4,5-dihydropyrazol-1-yl)benzene sulfonic acid; 4-(4-(1-(2-cyanoethyl)-1,2,3,4-tetrahydroquinolin-6-ylmethylene)-3-methyl-5-oxo-4,5-dihydropyrazol-1-yl)benzene sulfonic acid; 4-(4-(3-(4-dimethylaminophenyl)allylidene)-3-methyl-5-oxo-4,5-dihydropyrazol-1-yl)benzenesulfonic acid; ammonium 4-(4-(3-(4-dimethylaminophenyl)-allylidene)-3-methyl-5-oxo-4,5-dihydropyrazol-1-yl) benzene sulfonate; 4-(3-(4-dimethylaminophenyl) allylidene)-5-oxo-1-(4-sulfophenyl)-4,5-dihydro-1H-pyrazole-3-carboxylic acid; ammonium 4-(3-(4-dimethylaminophenyl)allylidene)-5-oxo-1-(4-sulfophenyl)-4,5-dihydro-1H-pyrazole-3-carboxylic acid; 3-(5-hydroxy-3-methyl-4-(2,4,6-trioxotetrahydropyrimidin-5-ylidenemethyl)pyrazol-1-yl)benzene sulfonic acid; 5-(1-(2,5-dichlorophenyl)-5-hydroxy-3-methyl-1H-pyrazol-4-ylmethylene)-2-thioxodihydropyrimidin-4,6-dione; 4-(4-(2,2-dimethyl-4,6-dioxo-[1,3]dioxane-5-ylidenemethyl)-5-hydroxy-3-methylpyrazol-1-yl)-benzene sulfonic acid; 4-(4-(5-(4,6-dioxo-1,3-dipropyl-2-thioxotetrahydro-pyrimidin-5-ylidene)penta-1,3-dienyl)-5-hydroxy-3-methylpyrazol-1-yl) benzene sulfonic acid; 2-(4-(4,4-bis-ethoxycarbonyl-1,3-butadienyl)-5-hydroxy-3-methyl-pyrazol-1-ylterephthalic acid, 1-(4-carboxyphenyl)-4-(4,4-dicarbamoyl-1,3-butadienyl)-5-hydroxy-1H-pyrazole-3-carboxylic acid; 2-(4-(2,2-bis-ethane-sulfonylvinyl)-5-hydroxy-3-methylpyrazol-1-yl)-terephthalic acid; 2-(3-methyl-5-oxo-1-phenyl-1,5-dihydropyrazol-4-ylidenemethyl)benzene sulfonic acid and sodium 2-(3-methyl-5-oxo-1-phenyl-1,5-dihydropyrazol-4-ylidenemethyl)benzene sulfonate.

9. The colorant as defined in claim 8, having a pH of from 2 to 11.

10. The colorant as defined in claim 8, further comprising a carrier.

11. The colorant as defined in claim 8, further comprising at least one polymer ingredient selected from the group consisting of natural polymers, synthetic polymers and modified polymers of natural origin.

12. A method of temporarily coloring and later decolorizing hair, said method comprising the steps of:
a) applying a hair colorant to the hair in an amount sufficient to color the hair;
b) after the applying of step a), allowing the hair colorant to remain on the hair for an exposure time of 10 to 45 minutes at 20 to 50° C.;
c) after the allowing of step b), rinsing the hair with water and subsequently drying the hair; and
d) after the rinsing and the drying of the hair, decolorizing the hair with a reducing agent or an oxidant at a later time as desired;
wherein said hair colorant comprises at least one dye compound of formula (IV), or a physiologically tolerated salt thereof;

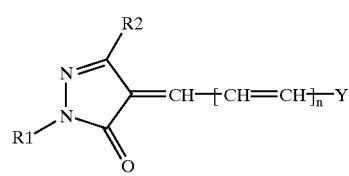

(IV)

wherein R1 represents hydrogen, a straight-chain or branched alkyl group containing one to eight carbon atoms, a hydroxyethyl group, a dihydroxypropyl group, a methoxyethyl group, a carboxy ethyl group, a sulfoalkyl group containing one to four carbon atoms, a phenyl radical, a phenyl radical substituted with at least one halogen atom, a phenyl radical substituted with one or two sulfonic acid groups, a phenyl radical substituted with at least one carboxylic acid group, a phenyl radical substituted with at least one straight-chain or branched alkyl group having one to eight carbon atoms, a phenyl radical substituted with at least one straight-chain or branched alkoxy group having one to eight carbon atoms, a benzyl radical, a benzyl radical substituted with at least one halogen atom, a benzyl radical substituted with an alkyl group having one to four carbon atoms, a benzyl radical substituted with a hydroxyl group, a benzyl radical substituted with a methoxy group, a benzyl radical substituted with a carboxyl group, a benzyl radical substituted with a nitro group, a benzyl radical substituted with an amino group or a five-membered or six-membered heterocyclic ring;

R2 represents hydrogen, a branched or straight-chain alkyl group having one to six carbon atoms, a phenyl radical, an amino group, an acylated amino group, a sulfonylated amino group, an acetyl group, a methoxy group, a carboxylic acid group, a carboxylic acid group esterified with a straight-chain or branched alcohol having one to eight carbon atoms, a carboxylic acid group esterified with ethylene glycol monomethyl ether, a carboxylic acid group esterified with ethylene glycol monoethyl ether, a carboxamido group, a carboxanilido group or a 2-amino-2-oxyethyl group; and Y represents an aromatic five-membered or six-membered carbocyclic or heterocyclic ring or a benzoanellated aromatic five-membered or six membered carbocyclic or heterocyclic ring, with no hydroxy group at an α position on said ring, or Y represents a radical of the formula (II) or (III):

wherein E1 and E2, independently of each other, each represent a nitrile group, an alkylsulfonyl group, acyl group, a carboxylate ester group or a carboxamido group; and n is 0, 1 or 2.

13. The method as defined in claim 12, further comprising washing the hair with a shampoo after the allowing of the hair colorant to remain on the hair.

14. The method as defined in claim 12, further comprising washing the hair with an aqueous solution of a weak organic acid after the allowing of the hair colorant to remain on the hair.

15. The method as defined in claim 12, wherein said reducing agent is an alkali metal sulfite, an alkali metal hydrogen sulfite, an alkali metal hyposulfite, an alkali metal metabisulfite, an ammonium sulfite or an ammonium hydrogen sulfite.

16. The method as defined in claim 15, wherein said reducing agent further comprises at least one member selected from the group consisting of reductones and thiols.

17. The method as defined in claim 12, wherein said oxidant is a bleaching powder containing from 5 to 50 percent by weight of at least one member selected from the group consisting of ammonium persulfate and alkali metal persulfate.

18. The method as defined in claim 12, wherein said oxidant is a combination of a hydrogen peroxide solution and a bleaching powder, said bleaching powder containing from 5 to 50 percent by weight of at least one member selected from the group consisting of ammonium persulfate and alkali metal persulfate.

19. A method of temporarily coloring and later decolorizing hair, said method comprising the steps of:

a) applying a hair colorant to the hair in an amount sufficient to color the hair;

b) after the applying of step a), allowing the hair colorant to remain on the hair for an exposure time of 10 to 45 minutes at 20 to 50° C.;

c) after the allowing of step b), rinsing the hair with water and subsequently drying the hair; and d) after the rinsing and the drying of the hair, decolorizing the hair with a reducing agent or an oxidant at a later time as desired;

wherein said hair colorant comprises at least one dye compound selected from the group consisting of 4-4(bis-(2-hydroxyethyl)-amino)benzylidene)-2-(2-hydroxyethyl)-5-methyl-2,4-dihydropyrazol-3-one; 2-(2-hydroxyethyl)-5-methyl-4-thiophen-2-yl-methylene-2,4-dihydropyrazol-3-one; 2-(2-hydroxyethyl)-5-methyl-4-thiophen-3-yl-methylene-2,4-dihydropyrazol-3-one; 4-(4-hydroxybenzylidene)-2-(2-hydroxyethyl)-5-methyl-2,4-dihydropyrazol-3-one, 4-(3-(4-dimethylaminophenyl)-allylidene)-2-(2-hydroxyethyl)-5-methyl-2,4-dihydropyrazol-3-one; 4-(4-(1H-indol-3-ylmethylene) 3-methyl-5-oxo-4,5-dihydropyrazol-1-yl)benzene sulfonic acid; triethylammonium-4-(4-(1H-indol-3-ylmethylene)-3-methyl-5-oxo-4,5-dihydropyrazol-1-yl)benzene sulfonate; 4-(4-di-methylaminobenzylidene)-5-oxo-1-(4-sulfophenyl)-4,5-dihydro-1H-pyrazole-3-carboxylic acid; ammonium 4-(4-dimethyl-aminobenzylidene)-5-oxo-1-(4-sulfophenyl)-4,5-dihydro-1H-pyrazole-3-carboxylic acid; 4-(4-(4-dimethyl-aminobenzylidene)-3-methyl-5-oxo-4,5-dihydro-pyrazol-1-yl)benzene sulfonic acid; ammonium 4-(4-(4-dimethylamino-benzylidene)-3-methyl-5-oxo-4,5-dihydropyrazol-1-yl)benzene sulfonate; 4-chloro-3-(4-(4-dimethylamino-benzylidene)-3-methyl-5-oxo-4,5-dihydropyrazol-1-yl)benzene sulfonic acid; ammonium 4-chloro-3-(4-(4-dimethylamino-benzylidene)-3-methyl-5-oxo-4,5-dihydropyrazol-1-yl)benzene sulfonate; 4-(4-(4-hydroxy-3-methoxybenzylidene)-3-methyl-5-oxo-4,5-dihydropyrazol-1-yl)benzene sulfonic acid; 4-(4-(4-methoxybenzylidene)-3-methyl-5-oxo-4,5-dihydropyrazol-1-yl)benzene sulfonic acid; 4-(4-(2,4-dimethoxybenzylidene)-3-methyl-5-oxo-4,5-dihydropyrazol-1-yl)benzene sulfonic acid; ammonium 4-(4-(2,4-dimethoxy-benzylidene)-3-methyl-5-oxo-4,5-dihydropyrazol-1-yl)benzene sulfonate; 4-(3-methyl-5-oxo-4-thiophen-2-ylmethylene4,5-dihydropyrazol-1-yl)benzene sulfonic acid; ammonium 4-(3-methyl-5-oxo4-thiophen-2-ylmethylene-4,5-dihydropyrazol-1-yl)benzene sulfonate; 4-(3-methyl-4-(1-methyl-1,2,3,4-tetrahydroquinolin-6-ylmethylene)-5-oxo-4,5-dihydropyrazol-1-yl)benzene sulfonic acid; 4-(4-(1-(2-cyanoethyl)-1,2,3,4-tetrahydroquinolin-6-ylmethylene)-3-methyl-5-oxo-4,5-dihydropyrazol-1-yl)benzene sulfonic acid; 4-(4-(3-(4-dimethylamino-phenyl)allylidene)-3-methyl-5-oxo-4,5-dihydropyrazol-1-yl)benzenesulfonic acid; ammonium 4-(4-(3-(4-dimethylaminophenyl)-allylidene)-3- methyl-5-oxo-4,5-dihydropyrazol-1-yl)benzene sulfonate; 4-(3-(4-dimethylaminophenyl)allylidene)-5-oxo-1-(4-sulfophenyl)4,5-dihydro-1H-pyrazole-3-carboxylic acid; ammonium 4-(3-(4-dimethylaminophenyl)allylidene)-5-oxo-1-(4-sulfophen-yl)-4,5-dihydro-1H-pyrazole-3-carboxylic acid; 3-(5-hydroxy-3-methyl-4-(2,4,6-trioxotetrahy- dropyrimidin-5-ylidenemethyl)pyrazol-1-yl)benzene sulfonic acid; 5-(1-(2,5-dichlorophenyl)-5-hydroxy-3-methyl-1H-pyrazol-4-ylmethylene)-2-thioxodihydropyrimidin-4,6-dione; 4-(4-(2,2-dimethyl-4,6-dioxo-[1,3]dioxane-5-ylidenemethyl)-5-hydroxy-3-methylpyrazol-1-yl)-benzene sulfonic acid; 4-(4-(5-(4,6-dioxo-1,3-dipropyl-2-thioxotetrahydro-pyrimidin-5-ylidene)penta-1,3-dienyl)-5-hydroxy-3-methylpyrazol-1-yl)benzene sulfonic acid; 2-(4-(4,4-bis-ethoxycarbonyl-1,3-butadienyl)-5-hydroxy-3-methyl-pyrazol-1-ylterephthalic acid, 1-(4-carboxyphenyl)4-(4,4-dicarbamoyl-1,3-butadienyl)-5-hydroxy-1H-pyrazole-3-carboxylic acid; 2-(4-(2,2-bis-ethane-sulfonylvinyl)-5-hydroxy-3-methylpyrazol-1-yl)-terephthalic acid; 2-(3-methyl-5-oxo-1-phenyl-1,5-dihydropyrazol-4-ylidenemethyl)benzene sulfonic acid and sodium 2-(3-methyl-5-oxo-1-phenyl-1,5-dihydropyrazol-4-ylidenemethyl)-benzene sulfonate.

20. The method as defined in claim 19, further comprising washing the hair with a shampoo after the allowing of the hair colorant to remain on the hair.

21. The method as defined in claim 19, further comprising washing the hair with an aqueous solution of a weak organic acid after the allowing of the hair colorant to remain on the hair.

22. The method as defined in claim 19, wherein said reducing agent is an alkali metal sulfite, an alkali metal hydrogen sulfite, an alkali metal hyposulfite, an alkali metal metabisulfite, an ammonium sulfite or an ammonium hydrogen sulfite.

23. The method as defined in claim 22, wherein said reducing agent further comprises at least one member selected from the group consisting of reductones and thiols.

24. The method as defined in claim 19, wherein said oxidant is a bleaching powder containing from 5 to 50 percent by weight of at least one member selected from the group consisting of ammonium persulfate and alkali metal persulfate.

25. The method as defined in claim 19, wherein said oxidant is a combination of a hydrogen peroxide solution and a bleaching powder, said bleaching powder containing from 5 to 50 percent by weight of at least one member selected from the group consisting of ammonium persulfate and alkali metal persulfate.

26. A method of coloring hair, said method comprising the steps of:
a) applying a hair colorant to the hair in an amount sufficient to color the hair;
b) after the applying of step a), allowing the hair colorant to remain on the hair for an exposure time of 10 to 45 minutes at 20° C. to 50° C.; and
c) after the allowing of step b), rinsing the hair with water and subsequently drying the hair;
wherein said hair colorant comprises at least one dye compound of formula (IV), or a physiologically tolerated salt thereof;

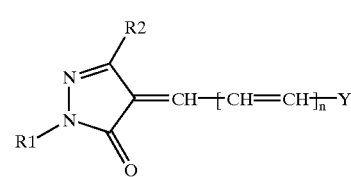

(IV)

wherein R1 represents hydrogen, a straight-chain or branched alkyl group containing one to eight carbon atoms, a hydroxyethyl group, a dihydroxypropyl group, a methoxyethyl group, a carboxy ethyl group, a sulfoalkyl group containing one to four carbon atoms, a phenyl radical, a phenyl radical substituted with at least one halogen atom, a phenyl radical substituted with one or two sulfonic acid groups, a phenyl radical substituted with at least one carboxylic acid group, a phenyl radical substituted with at least one straight-chain or branched alkyl group having one to eight carbon atoms, a phenyl radical substituted with at least one straight-chain or branched alkoxy group having one to eight carbon atoms, a benzyl radical, a benzyl radical substituted with at least one halogen atom, a benzyl radical substituted with an alkyl group having one to four carbon atoms, a benzyl radical substituted with a hydroxyl group, a benzyl radical substituted with a methoxy group, a benzyl radical substituted with a carboxyl group, a benzyl radical substituted with a nitro group, a benzyl radical substituted with an amino group or a five-membered or six-membered heterocyclic ring;

R2 represents hydrogen, a branched or straight-chain alkyl group having one to six carbon atoms, a phenyl radical, an amino group, an acylated amino group, a sulfonylated amino group, an acetyl group, a methoxy group, a carboxylic acid group, a carboxylic acid group esterified with a straight-chain or branched alcohol having one to eight carbon atoms, a carboxylic acid group esterified with ethylene glycol monomethyl ether, a carboxylic acid group esterified with ethylene glycol monoethyl ether, a carboxamido group, a carboxanilido group or a 2-amino-2-oxyethyl group; and Y represents an aromatic five-membered or six-membered carbocyclic or heterocyclic ring or a benzoanellated aromatic five-membered or six membered carbocyclic or heterocyclic ring, with no hydroxy group at an α position on said ring, or Y represents a radical of the formula (II) or (III):

wherein E1 and E2, independently of each other, each represent a nitrile group, an alkylsulfonyl group, acyl group, a carboxylate ester group or a carboxamido group; and n is 0, 1 or 2.

27. The method as defined in claim 26, further comprising washing the hair with a shampoo after the allowing of the hair colorant to remain on the hair.

28. The method as defined in claim 26, further comprising washing the hair with a weak organic acid after the allowing of the hair colorant to remain on the hair.

29. A method of coloring hair, said method comprising the steps of:
- a) applying a hair colorant to the hair in an amount sufficient to color the hair;
- b) after the applying of step a), allowing the hair colorant to remain on the hair for an exposure time of 10 to 45 minutes at 20° C. to 50° C.; and
- c) after the allowing of step b), rinsing the hair with water and subsequently drying the hair;
- wherein said hair colorant comprises at least one dye compound selected from the group consisting of selected from the group consisting of 4-4(bis-(2-hydroxyethyl)-amino)benzylidene)-2-(2-hydroxy-ethyl)-5-methyl-2,4-dihydropyrazol-3-one;2-(2-hydroxyethyl)-5-methyl-4-thiophen-2-yl-methylene-2,4-dihydropyrazol-3-one; 2-(2-hydroxyethyl)-5-methyl-4-thiophen-3-yl-methylene-2,4-dihydropyrazol-3-one; 4-(4-hydroxybenzylidene)-2-(2-hydroxy-ethyl)-5-methyl-2,4-dihydropyrazol-3-one, 4-(3-(4-dimethylaminophenyl)-allylidene)-2-(2-hydroxyethyl)-5-methyl-2,4-dihydropyrazol-3-one; 4-(4-(1H-indol-3-ylmethylene) 3-methyl-5-oxo-4,5-dihydropyrazol-1-yl)benzene sulfonic acid; triethylammonium-4-(4-(1H-indol-3-ylmethylene)-3-methyl-5-oxo-4,5-dihydropyrazol-1-yl)benzene sulfonate; 4-(4-di-methylaminobenzylidene)-5-oxo-1-(4-sulfophenyl)-4,5-dihydro-1H-pyrazole-3-carboxylic acid; ammonium 4-(4-dimethyl-aminobenzylidene)-5-oxo-1-(4-sulfophenyl)-4,5-dihydro-1H-pyrazole-3-carboxylic acid; 4-(4-(4-dimethyl-aminobenzylidene)-3-methyl-5-oxo-4,5-dihydropyrazol-1-yl)benzene sulfonic acid; ammonium 4-(4-(4-dimethylamino-benzylidene)-3-methyl-5-oxo-4,5-dihydropyrazol-1-yl)benzene sulfonate; 4-chloro-3-(4-(4-dimethylamino-benzylidene)-3-methyl-5-oxo-4,5-dihydropyrazol-1-yl)benzene sulfonic acid; ammonium 4-chloro-3-(4-(4-dimethylamino-benzylidene)-3-methyl-5-oxo-4,5-dihydropyrazol-1-yl)benzene sulfonate; 4-(4-(4-hydroxy-3-methoxybenzylidene)-3-methyl-5-oxo-4,5-dihydropyrazol-1-yl)benzene sulfonic acid; 4-(4-(4-methoxybenzylidene)-3-methyl-5-oxo-4,5-dihydropyrazol-1-yl)benzene sulfonic acid; 4-(4-(2,4-dimethoxybenzylidene)-3-methyl-5-oxo-4,5-dihydropyrazol-1-yl)benzene sulfonic acid; ammonium 4-(4-(2,4-dimethoxybenzylidene)-3-methyl-5-oxo-4,5-dihydropyrazol-1-yl)benzene sulfonate; 4-(3-methyl-5-oxo-4-thiophen-2-ylmethylene-4,5-dihydropyrazol-1-yl)benzene sulfonic acid; ammonium 4-(3-methyl-5-oxo-4-thiophen-2-ylmethylene-4,5-dihydropyrazol-1-yl)benzene sulfonate; 4-(3-methyl-4-(1-methyl-1,2,3,4-tetrahydroquinolin-6-ylmethylene)-5-oxo-4,5-dihydropyrazol-1-yl)benzene sulfonic acid; 4-(4-(1-(2-cyanoethyl)-1,2,3,4-tetrahydroquinolin-6-ylmethylene)-3-methyl-5-oxo-4,5-dihydropyrazol-1-yl)benzene sulfonic acid; 4-(4-(3-(4-dimethylamino-phenyl)allylidene)-3-methyl-5-oxo-4,5-dihydropyrazol-1-yl)benzenesulfonic acid; ammonium 4-(4-(3-(4-dimethylaminophenyl)-allylidene)-3-methyl-5-oxo-4,5-dihydropyrazol-1-yl)benzene sulfonate; 4-(3-(4-dimethylaminophenyl)allylidene)-5-oxo-1-(4-sulfophenyl)-4,5-dihydro-1H-pyrazole-3-carboxylic acid; ammonium 4-(3-(4-dimethylaminophenyl)allylidene)-5-oxo-1-(4-sulfophen-yl)-4,5-dihydro-1H-pyrazole-3-carboxylic acid; 3-(5-hydroxy-3-methyl-4-(2,4,6-trioxotetrahydro-pyrimidin-5-ylidenemethyl)pyrazol-1-yl)benzene sulfonic acid; 5-(1-(2,5-dichlorophenyl)-5-hydroxy-3-methyl-1H-pyrazol-4-ylmethylene)-2-thioxodihydropyrimidin-4,6-dione; 4-(4-(2,2-dimethyl-4,6-dioxo-[1,3]dioxane-5-ylidenemethyl)-5-hydroxy-3-methylpyrazol-1-yl)-benzene sulfonic acid; 4-(4-(5-(4,6-dioxo-1,3-dipropyl-2-thioxotetrahydro-pyrimidin-5-ylidene)penta-1,3-dienyl)-5-hydroxy-3-methylpyrazol-1-yl) benzene sulfonic acid; 2-(4-(4,4-bis-ethoxycarbonyl-1,3-butadienyl)-5-hydroxy-3-methyl-pyrazol-1-ylterephthalic acid, 1-(4-carboxyphenyl)-4-(4,4-dicarbamoyl-1,3-butadienyl)-5-hydroxy-1H-pyrazole-3-carboxylic acid; 2-(4-(2,2-bis-ethane-sulfonylvinyl)-5-hydroxy-3-methylpyrazol-1-yl)-terephthalic acid; 2-(3-methyl-5-oxo-1-phenyl-1,5-dihydropyrazol4-ylidenemethyl)benzene sulfonic acid and sodium 2-(3-methyl-5-oxo-1-phenyl-1,5-dihydropyrazol-4-ylidenemethyl)benzene sulfonate.

30. The method as defined in claim 29, further comprising washing the hair with a shampoo after the allowing of the hair colorant to remain on the hair.

31. The method as defined in claim 29, further comprising washing the hair with a weak organic acid after the allowing of the hair colorant to remain on the hair.

\* \* \* \* \*